United States Patent
Hu et al.

(10) Patent No.: US 10,239,823 B2
(45) Date of Patent: Mar. 26, 2019

(54) PROCESS FOR PURIFYING LONG CHAIN AMINO ACIDS

(71) Applicant: VITAWORKS IP, LLC, North Brunswick, NJ (US)

(72) Inventors: Songzhou Hu, Princeton, NJ (US); William S. Hu, Princeton, NJ (US)

(73) Assignee: VITAWORKS IP, LLC, North Brunswick (*) Notice: Subject to any disclaimer, the term of this patent is extended or adjusted under 35 U.S.C. 154(b) by 0 days.

(21) Appl. No.: 15/686,500

(22) Filed: Aug. 25, 2017

(65) Prior Publication Data
US 2019/0062265 A1 Feb. 28, 2019

(51) Int. Cl.
C07C 227/40 (2006.01)
C07C 227/42 (2006.01)

(52) U.S. Cl.
CPC .......... *C07C 227/40* (2013.01); *C07C 227/42* (2013.01)

(58) Field of Classification Search
CPC .................... C07C 227/40; C07C 227/42
USPC ................................................ 554/114
See application file for complete search history.

(56) References Cited

U.S. PATENT DOCUMENTS

| | | |
|---|---|---|
| 2,462,855 A | 3/1949 | Genas |
| 2,674,607 A | 4/1954 | Genas |
| 5,434,307 A | 7/1995 | Nwaonicha |
| 5,498,733 A | 3/1996 | Ayorinde |
| 5,530,148 A | 6/1996 | Nwaonicha |

FOREIGN PATENT DOCUMENTS

| | | |
|---|---|---|
| CN | 103804209 A | 5/2014 |
| GB | 953621 A | 3/1962 |

OTHER PUBLICATIONS

Perkins, R. B., et al., "Nylon-9 from unsaturated fatty derivatives: Preparation and characterization"; J. Am. Oil Chemist's Soc., Nov. 1975, vol. 52, Issue 11, pp. 473-477.
Kohlhase, W. L. et al., "9-Aminononanamide and nylon-9 from azelaaldehydic derivatives of soybean oil"; J. Am. Oil Chemist's Soc., 1970, vol. 47, No. 5, pp. 183-188; ISSN:0003-021X.
Miller, W. R. et al,; "Nylon-9 via 9-Aminononanoic Acid from Soybean Oil"; Ind. Eng. Chem. Prod. Res. Develop., 1971, vol. 10, pp. 442-447; DOI: 10.1021/i360040a022; Publication Date: Dec. 1971.
International Search Report and Written Opinion issued for International Patent Application No. PCT/US2018/039141 dated Oct. 18, 2018.

*Primary Examiner* — Deborah D Carr
(74) *Attorney, Agent, or Firm* — Myers Wolin, LLC

(57) ABSTRACT

There is disclosed a process for the purification of long chain amino acids by recrystallization in an aqueous solution of organic carboxylic acid in the absence or presence of solvent, comprising: (1) dissolving a long chain amino acid in an aqueous solution of organic carboxylic acid by heating; (2) cooling the solution of step (1) to crystallize the long chain amino acid; and (3) recovering the long chain amino acid of step (2) by means of solid-liquid separation.

19 Claims, 3 Drawing Sheets

PROCESS FOR PURIFYING LONG CHAIN AMINO ACIDS

TECHNICAL FIELD

The present invention relates to a process for the purification of long chain amino acids, more specifically, it relates to a process for the recrystallization of long chain amino acids in an aqueous solution of an acid.

BACKGROUNDS OF THE INVENTION

Long chain saturated aliphatic amino acids are important intermediates for the production of long chain nylons. Because of their unusual molecular structure, long chain nylons possess extraordinary physical properties, i.e., higher mechanical strength than metal, low hygroscopicity, excellent resistance to oil, low temperature, abrasion, and chemical corrosion, and most importantly, easy to fabricate. Long chain nylons are made into many kinds of plastics products, spun to fibers and stretched to thin films. Long chain nylons are also used in paints and hot melt adhesives. Hence, long chain nylons find wide applications in automobile, electrical, electronic, telecommunications, petrochemical, and aerospace industries.

Long chain amino acids, especially 9-aminononanoic acid and 11-aminoundecanoic acid, are used industrially as a monomer to produce nylong-9 and nylon-11, respectively. In addition, long chain amino acid, 12-aminolauric acid, may be used to produce an industrially important nylon-12, which is currently produced from laurolactam.

For the long chain amino acids to be used in the process to produce polyamide or nylons, they have to be refined to a grade suitable for polymerization. There are several known methods to achieve such purification.

In the first process, long chain amino acids are purified by recrystallization in water. U.S. Pat. No. 2,462,855 describes such a process to refine the crude 11-aminoundecanoic acid. In the disclosed process, 53 parts of the long chain amino acid is obtained from 1,500 parts of water. Through the concentration of mother liquor, 4 parts of additional long chain amino acid is recovered. Recrystallization from such dilute solution is not economical and energy-intensive to concentrate the mother liquor.

China Patent Appl. No. 103804209A describes a process to dissolve 11-aminoundecanoic acid in boiling water of ten times the amount of the amino acid to perform recrystallization. In light of the disclosure of U.S. Pat. No. 2,462,855 and the solubility property of the amino acid, it is unlikely for the process to achieve a clear solution so that impurities can be removed by filtration during the recrystallization.

U.S. Pat. No 2,674,607 describes a method to purify 9-aminononanoic acid by recrystallization from boiling water.

In the second process, long chain amino acids are purified by recrystallization in aqueous ethanol solution. GB 953,621 discloses a process to purify 10-aminodecanoic acid by recrystallization of the crude amino acid in a 80% aqueous ethanol.

U.S. Pat. No. 5,498,733 describes a process to refine 11-aminoundecanoic acid by recrystallizing the crude amino acid first in water, then in aqueous ethanol (3:1 of ethanol:water). The amount of water and aqueous ethanol used in the recrystallization are 122 times and 62 times the weight of the amino acid, respectively.

U.S. Pat. No. 5,434,307 and U.S. Pat. No. 5,530,148 describe a process to recrystallize 12-aminododecanoic acid in aqueous ethanol (1:1 of ethanol:water) in a recovery yield of 87%.

In the third process, 9-aminononanoic acid is purified by recrystallization in aqueous acetone solution. Kohlhase et al (J. Am. Oil Chemist's Soc., 1970, Vol. 47, pp183-188) describe a method to recrystallize the crude product of 9-aminononanoic acid in an aqueous solution of acetone (50%) with a recovery yield of 74%. The solvent is 130 times the weight of crude 9-aminononanoic acid.

Perkins et al (J. Am. Oil Chemist's Soc., 1975, Vol. 52, pp473-477) report an improvement of Kohlhase et al by first dissolving the crude 9-aminononanoic acid in hot water to form a 10% solution, followed by treatment with activated carbon and Cellite. After filtration, the solution is cooled and then mixed with an equal volume of acetone to precipitate the amino acid. Perkins et al further note that the amino acid crystallizes from water or water-acetone mixture as fine hydrophilic crystals, which contain the mother liquor. The crude amino acid has to be recrystallized often twice to obtain a product suitable for polymerization.

Finally, Miller et al (Ind. Eng. Chem. Prod. Res. Develop., 1971, Vol. 10, pp442-447) have studied in detail the purification of 9-aminononanoic acid by comparing the precipitation process from an aqueous solution by using acetone, tetrahydrofuran, or dimethylformamide. A large quantity of organic solvents is required to precipitate 9-aminononanoic acid.

In general, the process of recrystallization in a suitable solvent is required to obtain a long chain amino acid that is suitable for polymerization to produce polyamide or nylon. Since the solubility of long chain amino acids is small in water and organic solvent, a large amount of water or aqueous solvent is required to dissolve the long chain amino acid. Hence, the processes according to prior art require a large amount of energy to concentrate the mother liquor, to recover the solvent, and are not economical.

It is the object of the present invention to overcome the disadvantage of the known processes for the purification of long chain amino acids and to provide additional advantage, which will become apparent from the following description.

By the process according to the present invention, purification of long chain amino acids by recrystallization can be carried out at high concentration and long chain amino acids of high purity are obtained simply and economically on an industrial scale.

DESCRIPTION OF THE INVENTION

The present invention is related to a process for the purification of long chain amino acids by recrystallization from an aqueous solution of an acid. The long chain amino acids have the following structure:

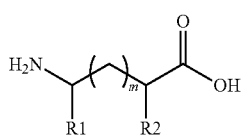

wherein m is integer from 6 to 20; $R_1$ and $R_2$ are each independently hydrogen or $C_1$-$C_{12}$ alkyl groups. The long chain amino acid can be a single compound or a mixture of two or more isomers.

In one embodiment of the present invention, a long chain amino acid is purified by recrystallization from an aqueous solution of organic carboxylic acid. Suitable carboxylic acid is selected from the group consisting of formic acid, acetic acid, propionic acid, butyric acid, glycolic acid, lactic acid, malic acid, tartaric acid, citric acid, and a mixture of two or more thereof. Preferably, the carboxylic acid is acetic acid or propionic acid. More preferably, the carboxylic acid is acetic acid.

Figure 1:
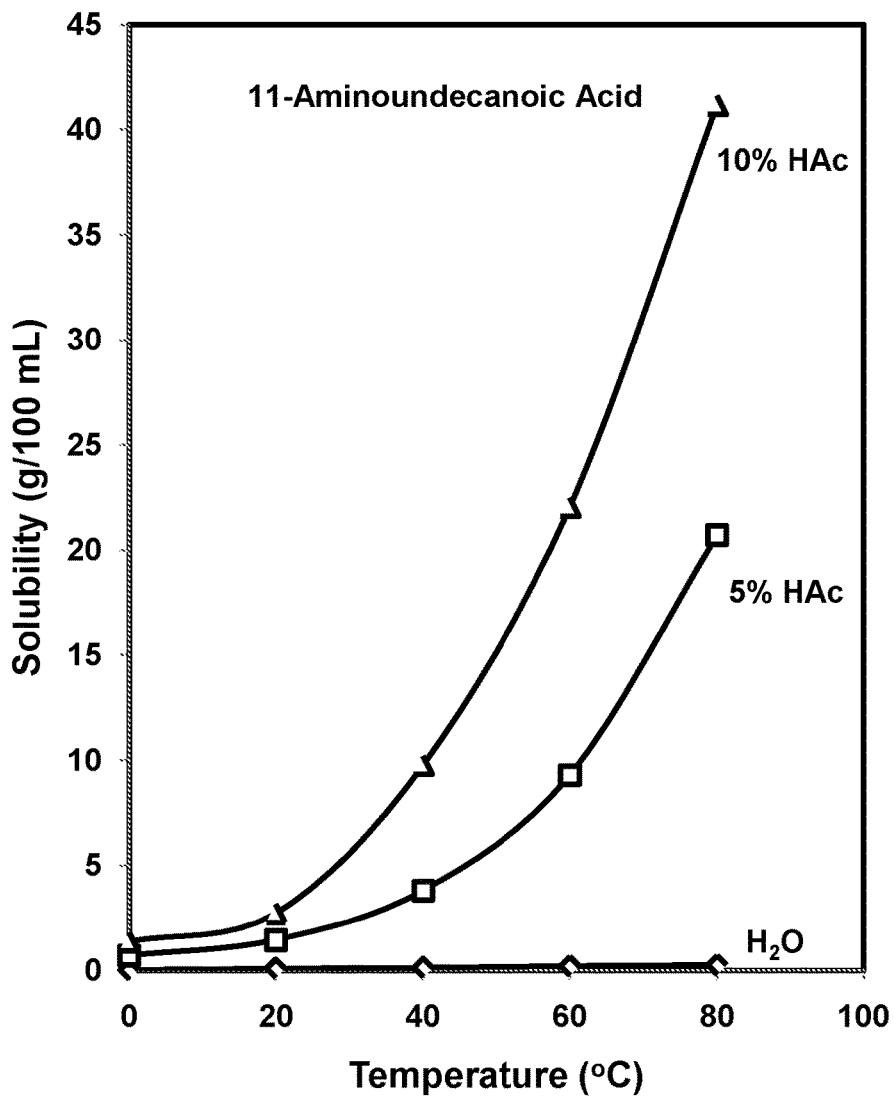
FIG. 1. Solubility curve of 11-aminoundecanoic acid in water and aqueous solution of acetic acid.
Figure 2:
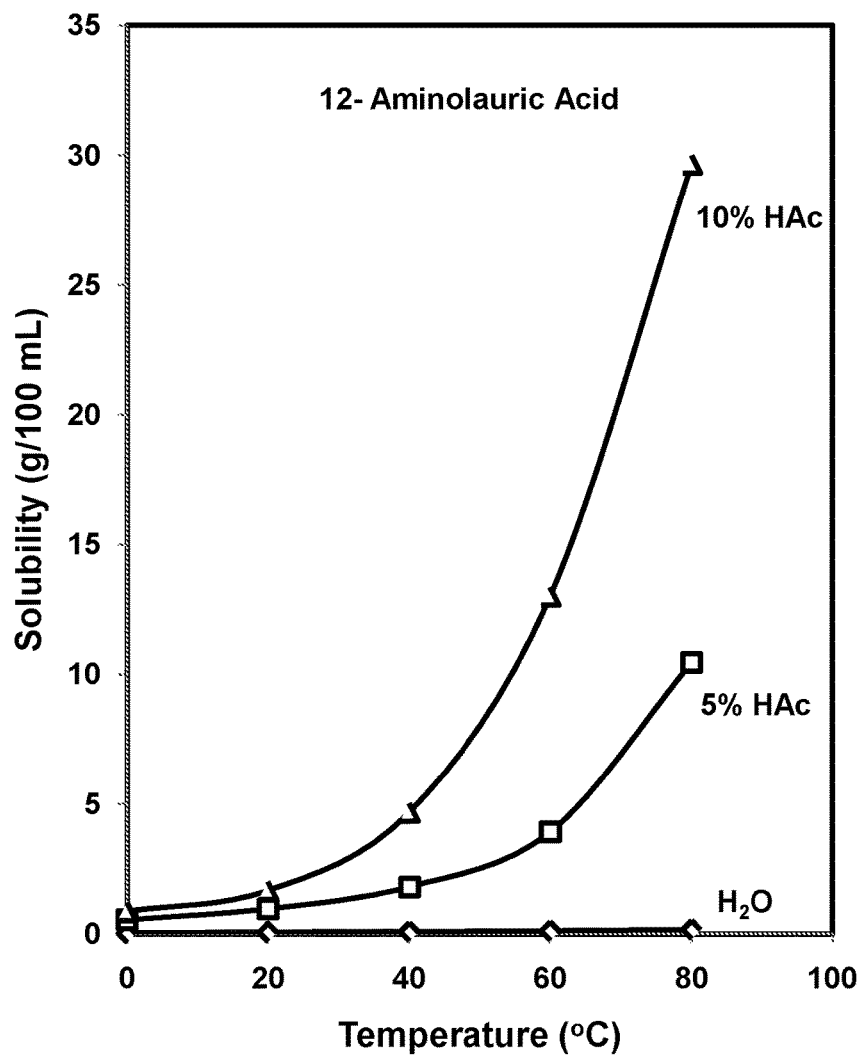
FIG. 2. Solubility curve of 12-aminolauric acid in water and aqueous solution of acetic acid.

It is surprising to have found that dilute acetic acid in water greatly increases the solubility of long chain amino acids, so that the recrystallization can be carried out at a high concentration. FIG. 1 and FIG. 2 show the solubility of 11-aminoundecanoic acid and 12-aminolauric acid in water and two different concentrations of acetic acid (5% and 10% wt/wt), respectively. It becomes apparent that the nearly insoluble long chain amino acids in water become soluble, for example, up to 45% (wt/wt) for 11-aminoundecanoic acid in an aqueous solution of only 10% (wt/wt) acetic acid at 80° C. Recrystallization at such a high concentration renders the process according to the present invention simple and economical on an industrial scale.

Although acetic acid greatly increases the solubility of long chain amino acids in water, acetic acid does not form an acid salt with these long chain amino acids. When 11-aminoundecanoic acid and 12-aminolauric acid are each recrystallized from deionized water and an aqueous solution containing 10% (wt/wt) acetic acid, the products show the same melting point as demonstrated in the Table 1. Little or no trace of acetic acid can be detected by GC analysis for products after thorough drying. When dissolved in water, the products, obtained from acidic solution of acetic acid remain neutral, thus no basic agent, i.e., alkali hydroxide or ammonium hydroxide, is needed to adjust the pH of the solution.

TABLE 1

Melting Point of Acid Salts of
11-Aminoundecanoic Acid and 12-Aminolauric Acid

| | 11-Aminoundecanoic Acid | 12-Aminolauric Acid |
|---|---|---|
| Water | 185-187° C. | 182-184° C. |
| Acetic Acid | 185-187° C. | 182-184° C. |
| Sulfuric Acid | 142-144° C. | 136-137° C. |
| Hydrochloric Acid | 141-143° C. | 155-157° C. |
| Nitric Acid | 68-74° C. | 67-72° C. |

In the process according to the present invention, crude long chain amino acid is purified by recrystallization from an aqueous solution of acetic acid. The content of acetic acid in water can be 1-95% (wt/wt), preferably 2-80% (wt/wt), more preferably 2-50% (wt/wt), most preferably 5-15% (wt/wt). When the content of acetic acid is too high, the recovery yield may be lowered.

The amount of aqueous acetic acid should be sufficient to dissolve the crude long chain amino acid and can be determined from the solubility curve by those skilled in the art. Thus the amount of aqueous acetic acid is 1-10 times, preferably 2-8 times, more preferably 3-5 times, the weight of crude long chain amino acid. When a larger amount of aqueous acetic acid is used in recrystallization, the recovery yield of long chain amino acid may be reduced.

The temperature to dissolve the long chain amino acid in aqueous acetic acid is from room temperature to the boiling point of the aqueous solution, preferably from 50 to 100° C., more preferably from 60 to 95° C., most preferably from 80-90° C.

After the crude long chain amino acid is dissolved, active carbon or filter aid may be added to remove colored material and to absorb impurities. After filtration at the preferable temperature, a clear solution is obtained.

Crystallization of the long chain amino acid is initiated by cooling the aqueous solution of acetic acid in a manner known to those skilled in the art. The crystalline suspension is further lowered to room temperature or lower to complete the crystallization.

The crystallized long chain amino acid is recovered by means of solid-liquid separation, i.e., filtration or centrifuge. The recovered solid material is washed with aqueous solution of acetic acid or with deionized water to yield a product of high purity.

The recrystallization process according to the present invention may be performed in an aqueous solution of acetic acid in the presence of solvent. Suitable solvent is selected from the group consisting of methanol, ethanol, propanol, isopropanol, tert-butanol, acetone, butanone, tetrahydrofuran, dioxane, dimethylformamide, dimethylacetamide, N-methylpyrrolidinone, and a mixture of two or more thereof. Addition of solvent in an aqueous solution of acetic acid may improve the quality of the product and help to remove impurities.

In another embodiment of the present invention, a long chain amino acid is purified through an intermediate acid salt, which is produced by the recrystallization of long chain amino acid in an aqueous solution of inorganic acid. Suitable acid is selected from the group consisting of sulfuric acid, hydrochloric acid, hydrobromic acid, nitric acid, phosphoric acid, and a mixture of two or more thereof. Preferably, the inorganic acid is sulfuric acid.

When 11-aminoundecanoic acid and 12-aminolauric acid are recrystallized from sulfuric acid, hydrochloric acid, and nitric acid, an acid salt is isolated in each case. These salts have their own characteristic melting point as shown in Table 1. These salts exhibit strong acidic property, when dissolved in water. Neutral amino acids can only be obtained by neutralization with a basic agent.

Figure 3:
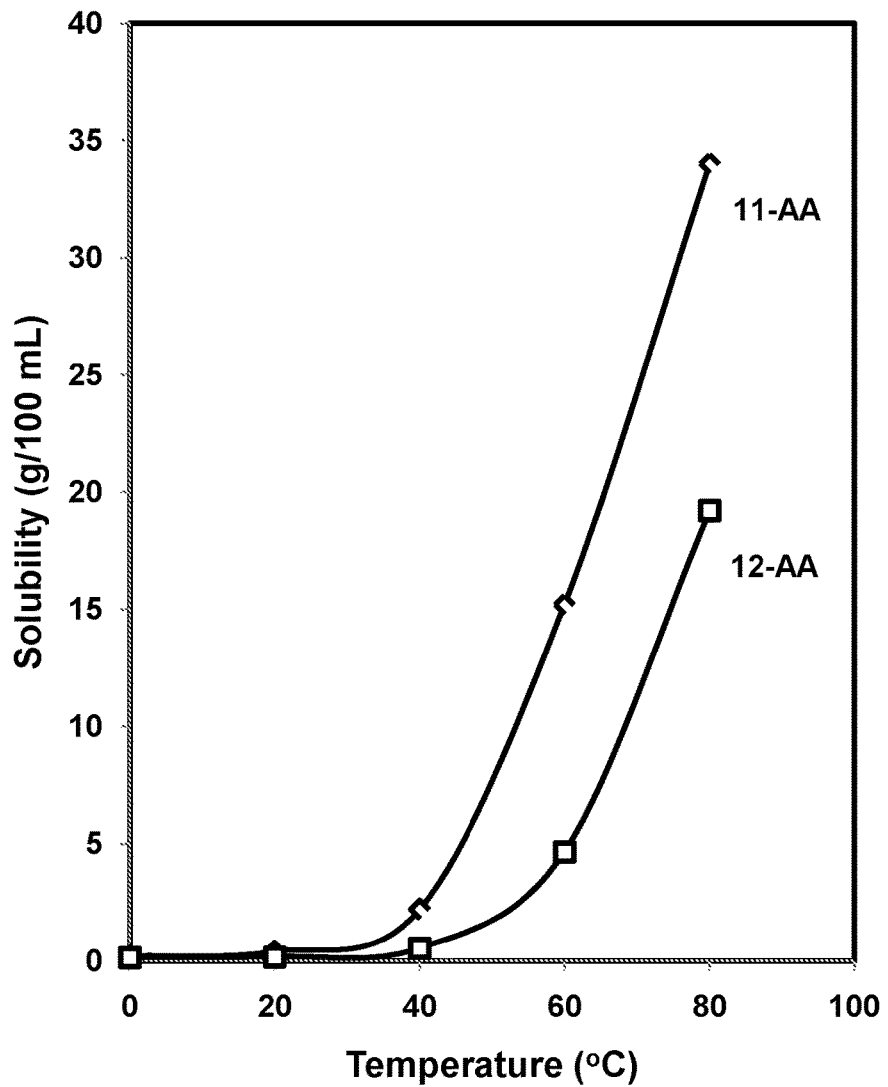
FIG. 3. Solubility curve of 11-aminoundecanoic acid (11-AA) and 12-aminolauric acid (12-AA) in 1 M solution of sulfuric acid.

FIG. 3 shows the solubility of the bisulfate salts of 11-aminoundecanoic acid and 12-aminolauric acid in 1 M solution of sulfuric acid. It is surprising to find that the bisulfate salts of these two long chain amino acids have negligible solubility at a temperature below 40° C., but their solubility is drastically increased as the temperature is increased from 60° C. to 80° C. and above. This solubility property of the bisulfate salts provides a simple and economical process for the purification of the crude long chain amino acids as the intermediate bisulfate salt can be isolated in high yield.

In the process according to the present invention, crude long chain amino acid is purified in the form of an intermediate acid salt by the recrystallization in an aqueous solution of inorganic acid, preferably, sulfuric acid. The molar ratio of sulfuric acid to the long chain amino acid is from 0.1 to 10, preferably from 0.5 to 5, more preferably from 0.5 to 2, most preferably from 0.9 to 1.1. Excess sulfuric acid is not necessary and is avoided in order to reduce or eliminate waste acid solution.

The amount of aqueous sulfuric acid is from 1 to 10 times, preferably from 2 to 5 times, more preferably 3 to 4 times, the weight of crude long chain amino acid. Too much solution may reduce the recovery yield of the long chain amino acid. The optimum amount may be determined by those skilled in art according to the solubility of the acid salt.

After a crude long chain amino acid is dissolved in an aqueous solution of sulfuric acid at a temperature form 50° C. to the boiling point, preferably from 60° C. to 95° C., most preferably from 80° C. to 90° C., activated carbon or filter aid may be added to decolorize and to absorb impurities. After filtration, a clear solution is obtained.

On the other hand, the sulfuric acid solution of crude long chain amino acid is treated with an organic extractant solvent to remove impurities. It is surprising that nearly all colored materials are transferred into the extractant phase, and the aqueous phase is nearly colorless.

Suitable extractant solvents are water-insoluble and belong to the classes of ester, aliphatics, aromatics, ethers, alcohols of $C_4$ to $C_{10}$, and ketones of $C_4$ to $C_{10}$. Useful solvents include, but not limited to, butyl formate, isobutyl formate, butyl acetate, isobutyl acetate, propyl acetate, isopropyl acetate, ethyl acetate, ethyl propionate, octyl acetate, benzene, toluene, xylene, cumene, anisole, diethyl ether, diisopropyl ether, dibutyl ether, methyl tert-butyl ether, ethyl tert-butyl ether, methyl tetrahydrofuran, petroleum ether, cyclohexane, dichloroethane, methylene chloride, chloroform, carbon tetrachloride, and trifluoromethylbenzene, n-butanol, isobutanol, amyl alcohol, isoamyl alcohol, hexanol, cyclohexanol, 2-ethylhexanol, isooctanol, sec-octanol, butanone, pentanone, hexanone, cyclohexanone, and methyl isobutyl ketone. A single solvent or a mixture of two or more solvents can be used as extractant solvent.

Preferably, the extractant solvent is toluene.

The clear solution after treatment with activated carbon or filtrate or extraction can be neutralized with a basic agent to a neutral pH in the range of 5 to 9, more preferably 6 to 8. The neutralization can be carried out at a temperature from room temperature to the boiling point of the solution, preferably from 50° C. to 90° C., more preferably from 70° C. to 80° C. At the more preferable temperature, the product has large crystal size, is easy to filtrate, and most importantly shows excellent purity In a further embodiment of the present invention, the clear solution after treatment with activated carbon or filter aid or extraction is cooled to start the crystallization of the acid salt of long chain amino acid in a manner known to those skilled in the art. The crystalline suspension is further lowered to room temperature or lower to complete the crystallization. The crystalline acid salt is then recovered by means of solid-liquid separation, i.e., filtration or centrifuge, and washed with water.

To recover the long chain amino acid, an acid salt is dissolved or suspended in water and neutralized with a basic agent to a neutral pH in the range of 5 to 9, more preferably 6 to 8. The neutralization can be carried out at a temperature from room temperature to the boiling point of the solution, preferably from 50° C. to 90° C., more preferably from 70° C. to 80° C. At the more preferable temperature, the product has large crystal size, is easy to filtrate, and most importantly shows excellent purity.

Suitable basic agent is selected from the group consisting of alkali and ammonium salts of hydroxide, bicarbonate, carbonate, bisulfite, sulfite, and a mixture of two or more thereof. Preferably, the basic agent is ammonia or ammonium hydroxide.

After the completion of neutralization, the crystalline suspension is cooled to room temperature to complete the crystallization. The neutral long chain amino acid is recovered by means of solid-liquid separation and washed with deionized water.

EXAMPLES

The following examples illustrate the practice of this invention but are not intended to limit its scope.

Example 1

To 100 mL solution of 10% (wt/wt) acetic acid was added 40 g of crude 11-aminoundecanoic acid and the suspension was heated to 90° C. to obtain a cloudy solution, to which 1 g of activated carbon was added. The solution was gently stirred at the same temperature for 1 hour and filtered through a layer of Cellite at the same temperature to obtain a clear and colorless solution. Upon slow cooling to room temperature, a crystalline mass was obtained. The crystalline product was filtered and washed three times with deionized water. After drying, 36 g of 11-aminoundecanoic acid was obtained with a purity of 99.6%.

Example 2

To 100 mL solution of 10% (wt/wt) acetic acid was added 30 g of crude 12-aminolauric acid and the suspension was heated to 90° C. to obtain a cloudy solution, to which 0.75 g of activated carbon was added. The solution was gently stirred at the same temperature for 1 hour and filtered through a layer of Cellite at the same temperature to obtain a clear and colorless solution. Upon slow cooling to room temperature, a crystalline mass was obtained. The crystalline product was filtered and washed three times with deionized water. After drying, 28 g of 11-aminoundecanoic acid was obtained with a purity of 99.7%.

Example 3

To 100 mL solution of 10% (wt/wt) acetic acid was added 40 g of a mixture of 11-aminoundecanoic acid (80% wt/wt) and 10-aminoundecanoic acid (20% wt/wt) and the suspension was heated to 90° C. to obtain a cloudy solution, to which 1 g of activated carbon was added. The solution was gently stirred at the same temperature for 1 hour and filtered through a layer of Cellite at the same temperature to obtain a clear and colorless solution. Upon slow cooling to room temperature, a crystalline mass was obtained. The crystalline product was filtered and washed three times with deionized water. After drying, 35 g of a mixture of 11-aminoundecanoic acid (83% wt/wt) and 10-aminoundecanoic acid (17% wt/wt) was obtained.

Example 4

To 100 mL solution of 1 M sulfuric acid was added 40 g of crude 11-aminoundecanoic acid and suspension was heated to 90° C. to obtain a cloudy solution, to which 50 mL of toluene was added and vigorously stirred for 1 hour. After phase separation, the aqueous phase was passed through a layer of Cellite to afford a clear and colorless solution. Upon cooling, a massive amount of bisulfate salt was formed and the suspension was cooled to room temperature.

The precipitate was filtered, washed with deionized water, then suspended again in 100 mL of deionized water. The suspension was warmed to 80° C. and neutralized by slow addition of 25% ammonium hydroxide to a pH of 6.8. After cooling to room temperature, crystalline solid 11-aminoundecanoic acid was obtained by filtration, washing with deionized water three times. After drying, the white product weighted 35 g and had a purity of 99.7%.

It will be understood that the foregoing examples, explanation, and drawings are for illustrative purpose only and that in view of the instant disclosure various modifications of the present invention will be self-evident to those skilled in the art and are to be included within the spirit and purview of this application and the scope of the claims.

What is claimed is:

1. A process for the purification of long chain amino acids of the following structure:

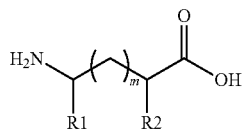

wherein m is integer from 6 to 20; $R_1$ and $R_2$ are each independently hydrogen and $C_1$-$C_{12}$ alkyl groups, by recrystallization in an aqueous solution of organic carboxylic acid in the absence or presence of solvent, comprising:
   (1) dissolving a long chain amino acid in an aqueous solution of organic carboxylic acid by heating;
   (2) cooling the solution of step (1) to crystallize the long chain amino acid; and
   (3) recovering the long chain amino acid of step (2) by means of solid-liquid separation.

2. A process for the purification of long chain amino acids of the following structure:

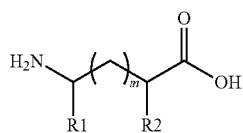

wherein m is integer from 6 to 20; $R_1$ and $R_2$ are each independently hydrogen and $C_1$-$C_{12}$ alkyl groups, by recrystallization in an aqueous solution of inorganic acid, comprising:
   (1) dissolving a long chain amino acid in an aqueous solution of inorganic acid by heating;
   (2) treating the solution of step (1) with activated carbon, or filter aid, or an extractant solvent;
   (3) cooling the solution of step (2) to crystallize the acid salt of the long chain amino acid;
   (4) separating the acid salt of step (3) by means of solid-liquid separation; and
   (5) neutralizing the acid salt of step (4) with a basic agent to yield the long chain amino acid.

3. A process for the purification of long chain amino acids of the following structure:

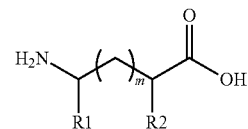

wherein m is integer from 6 to 20; $R_1$ and $R_2$ are each independently hydrogen and $C_1$-$C_{12}$ alkyl groups, by forming an acid salt in an aqueous solution of inorganic acid, comprising:
   (1) dissolving a long chain amino acid in an aqueous solution of inorganic acid by heating to form an acid salt;
   (2) treating the solution of step (1) with activated carbon, or filter aid, or an extractant solvent; and
   (3) neutralizing the solution of step (2) with a basic agent to yield the long chain amino acid.

4. The process according to claim 1, wherein the organic carboxylic acid is selected from the group consisting of formic acid, acetic acid, propionic acid, butyric acid, glycolic acid, lactic acid, malic acid, tartaric acid, citric acid, and a mixture of two or more thereof.

5. The process according to claim 1, wherein the aqueous solution of organic carboxylic acid is aqueous acetic acid.

6. The process according to claim 5, wherein the content of acetic acid in the aqueous solution is from 2% to 95% (wt/wt).

7. The process according to claim 5, wherein the aqueous acetic acid solution of crude long chain amino acid is treated with activated carbon or filter aid to remove impurities.

8. The process according to claim 1, wherein the solvent is selected from the group consisting of methanol, ethanol, propanol, isopropanol, tert-butanol, acetone, butanone, tetrahydrofuran, dioxane, dimethylformamide, dimethylacetamide, N-methylpyrrolidinone, and a mixture of two or more thereof.

9. The process according to claim 1, wherein the long chain amino acids are 9-aminononanoic acid, 10-aminoundecanoic acid, 11-aminoundecanoic acid, 12-aminolauric acid, 9-aminodecanoic acid, 10-aminodecanoic acid, or a mixture of two or more isomers.

10. The process according to claim 2, wherein the inorganic acid is selected from the group consisting of sulfuric acid, hydrochloric acid, hydrobromic acid, nitric acid, phosphoric acid, and a mixture of two or more thereof.

11. The process according to claim 2, wherein the inorganic acid is sulfuric acid.

12. The process according to claim 2, wherein the molar ratio of the inorganic acid to long chain amino acid is from 0.1 to 10.

13. The process according to claim 2, wherein the molar ratio of the inorganic acid to long chain amino acid is from 0.9 to 1.1.

14. The process according to claim 2, wherein the aqueous solution of the acid salt of crude long chain amino acid is treated with activated carbon or filter aid to remove impurities.

15. The process according to claim 2, wherein the aqueous solution of the acid salt of crude long chain amino acid is treated with an extractant solvent to remove impurities.

16. The process according to claim 2, wherein the extractant solvent is selected from the group consisting of butyl formate, isobutyl formate, butyl acetate, isobutyl acetate, propyl acetate, isopropyl acetate, ethyl acetate, ethyl propionate, octyl acetate, benzene, toluene, xylene, cumene, anisole, diethyl ether, diisopropyl ether, dibutyl ether, methyl tert-butyl ether, ethyl tert-butyl ether, methyl tetrahydrofuran, petroleum ether, cyclohexane, dichloroethane, methylene chloride, chloroform, carbon tetrachloride, and trifluoromethylbenzene, n-butanol, isobutanol, amyl alcohol, isoamyl alcohol, hexanol, cyclohexanol, 2-ethylhexanol, isooctanol, sec-octanol, butanone, pentanone, hexanone, cyclohexanone, methyl isobutyl ketone, and a mixture of two or more thereof.

17. The process according to claim 2, wherein the extractant solvent is toluene.

18. The process according to claim 2, wherein the basic agent is selected from the group consisting of alkali and ammonium salts of hydroxide, bicarbonate, carbonate, bisulfite, sulfite, and a mixture of two or more thereof.

19. The process according to claim 2, wherein the basic agent is ammonia or ammonium hydroxide.

* * * * *